United States Patent [19]
Kobayashi et al.

[11] 3,954,856
[45] May 4, 1976

[54] METHOD FOR VAPOR-PHASE CATALYTIC OXIDATION OF TERT.-BUTYL ALCOHOL

[75] Inventors: Masao Kobayashi; Hideo Matsuzawa, both of Ohtake; Kantaro Yamada, Yokohama; Hiromichi Ishii, Ohtake, all of Japan

[73] Assignee: Mitsubishi Rayon Company, Ltd., Tokyo, Japan

[22] Filed: Aug. 29, 1974

[21] Appl. No.: 501,681

[30] Foreign Application Priority Data
- Aug. 29, 1973  Japan.............................. 48-96948
- Dec. 18, 1973  Japan.............................. 48-142119
- Dec. 20, 1973  Japan.............................. 48-1151

[52] U.S. Cl. ........................ 260/533 N; 252/437; 252/439; 260/531 R; 260/604 R
[51] Int. Cl.² ................. C07C 51/26; C07C 45/16
[58] Field of Search .................... 260/533 N, 604 R

[56] References Cited
UNITED STATES PATENTS

| | | | |
|---|---|---|---|
| 3,470,239 | 9/1969 | Russell | 260/604 R |
| 3,642,930 | 2/1972 | Cranelli et al. | 260/533 N |
| 3,829,476 | 8/1974 | Yamada et al. | 260/533 N |

FOREIGN PATENTS OR APPLICATIONS

| | | | |
|---|---|---|---|
| 47-6606 | 2/1972 | Japan | 260/533 N |

OTHER PUBLICATIONS

March, *Advanced Organic Chemistry* (1968) pp. 753–755.

*Primary Examiner*—Anton H. Sutto
*Attorney, Agent, or Firm*—Oblon, Fisher, Spivak, McClelland & Maier

[57] ABSTRACT

Oxidation of tert.-butyl alcohol is accomplished by contacting said alcohol with a tungsten-molybdenum-tellurium-nickel catalyst in the vapor phase at an elevated temperature in the presence of oxygen, in order to produce methacrolein and methacrylic acid. The catalyst desirably contains phosphorus and/or antimony in addition to the elements mentioned above.

6 Claims, No Drawings

METHOD FOR VAPOR-PHASE CATALYTIC OXIDATION OF TERT.-BUTYL ALCOHOL

Methacrolein is a useful substance as it is and also as an intermediate for the production of methacrylic acid. It has long been well known to obtain methacrolein by the vapor-phase catalytic oxidation of isobutylene. However, the method of obtaining methacrolein from tert.-butyl alcohol is not quite so popular.

Official Gazette of Japanese Patent Publication No. 16858/1966 discloses that methacrolein is obtained in one step when tert.-butyl alcohol is reacted with air in the vapor phase in the presence of steam over a catalyst such as of phosphomolybdic acid carried on alumina or silicon carbide. In this process, however, methacrolein and methacrylic acid are obtained in yields not exceeding 30% and therefore has much yet to be improved.

Official Gazette of Japanese Patent Laying Open No. 32814/1973 discloses a process for effecting the vapor-phase catalytic oxidation of tert.-butyl alcohol by use of a catalyst having a specific composition containing thallium. The catalyst involved in this disclosure gives fairly favorable reaction results. When thallium, a poisonous element, is removed from this catalyst, the yield of methacrolein falls to the level of abot 40%, rendering the process commercially infeasible.

The inventors pursued an extensive research for a process capable of obtaining methacrolein and methacrylic acid from tert.-butyl alcohol in yields quite satisfactory from the commerical point of view. It has been discovered, consequently, that a catalyst of the Mo—W—Te system meets the purpose satisfactorily. This invention has been accomplished on this discovery.

It is an object of this invention to provide a catalyst capable of producing methacrolein and methacrylic acid from tert.-butyl alcohol in high yields and further a method for producing methacrolein and methacrylic acid in high yields.

This invention relates to a method for the production of methacrolein and methacrylic acid, which comprises contacting a mixed gas containing tert.-butyl alcohol and oxygen with a catalyst having the following composition in the vapor phase at a temperatures in the range from 200° to 500°C:

$$P_a W_b Mo_c Te_d Sb_e Sn_f R_g X_h Y_i O_j$$

wherein, R represents one of the combinations (a) Ni and Co, (b) Ni and Fe, (c) Ni, Co and Bi and (d) Ni, Fe and Bi; X represents K, Rb and/or Cs; Y represents Pd, U, Ge and/or Ti; $a, b, c, d, e, f, g, h, i$ and $j$ represent the numbers of atoms of the respective elements; and if $b + c = 1$, then $a = 0 - 1$, preferably 0.02 – 0.3, $d = 0.001 - 1$, preferably 0.01 – 0.2, $e = 0 - 1$, preferably 0.01 – 0.8, $f = 0 - 1$, preferably 0.02 – 0.9, $g = 0.08 - 2$, preferably 0.1 – 1.6, $h = 0 - 0.6$, preferably 0.0005 – 0.5, = 0 – 2, preferably 0.01 – 1.6, and $j$ is a value automatically determined by the valencies of the metallic oxides present therein, the ratio of $b$ to $c$ is 0.01 – 100 and the number of atoms of the two or three individual elements constituting R falls in the scope of 0.02 – 1, when $b + c = 1$.

When the reaction is effected in accordance with the present invention, a small amount of methacrylic acid is obtained together with methacrolein. These compounds are both useful. The form in which each of the components of the catalyst used for the present invention exists is not specifically limited. Thus, the catalyst may be a mixture of the oxides of the individual metallic elements. Preferably, the catalyst may as well be an oxide by having the elements combined altogether in some form or other.

When the catalyst contains antimony, yields of methacrolein and methacrylic acid are considerably better than when there is used a catalyst containing no antimony. When the catalyst contains tin, the life thereof is longer than when there is contained no tin.

The catalyst of the present invention can be carried on any of the known carriers such as silica gel, silica-alumina, corundum, silicon carbide and perlite.

In the preparation of the catalyst, any of the conventionally known techniques may practically be used. For example, an aqueous solution or suspension of the raw materials for catalyst is evaporated to dryness and the resultant cake is calcined in the air. The raw materials for the catalyst are desired to be in the form of metals, oxides, chlorides, or in the form of such compounds as acids, ammonium salts or nitrates which are converted into oxides by calcination. It is also permissible to use raw materials of such type as ammonium phosphomolybdate and stannomolybdic acid which have different component elements chemically combined. The calcination of the catalyst is carried out at temperatures of 250° – 700°C, preferably 350° – 600°C.

The reaction can be carried out by any suitable method, such as the fixed bed method or fluidized bed method, for example.

The concentration of tert.-butyl alcohol and that of oxygen in the mixed gas as the starting material are desirable in the range of 1 – 20 vol%, preferably 3 – 15 vol%. Desirably the mixed gas may suitably be diluted such as with nitrogen, steam, carbon dioxide, butane or the like to have these concentrations kept in said range.

The reaction temperature is desirable in the range of 200° – 500°C, preferably 300° – 400°C. The space velocity of the feed gas is desirable in the range of 500 – 7,000 lit./lit./hr. The reaction can be carried out at either normal or increased pressure.

The effect of the present invention will be described in further detail herein below with reference to preferred embodiments, which are illustrative of the invention and not in any way limitative of the scope of this invention. In the following examples, parts are those by weight and the total per-pass yield of methacrolein and methacrylic acid represents the value calculated as shown below:

Per-pass yield(%) = $\dfrac{\text{Total number of mols of methacrolein and methacrylic acid obtained}}{\text{Number of mols of tert.-butyl alcohol supplied}} \times 100$

EXAMPLE 1

In 600 parts of water, 38.5 parts of ammonium paratungstate was dissolved by boiling. To the resultant solution were added a solution having 5.0 parts of ammonium paramolybdate dissolved in 50 parts of water, a solution having 2.7 parts of cobalt nitrate and 2.8 parts of nickel nitrate dissolved in 100 parts of water and a solution having 1.71 parts of potassium nitrate dissolved in 10 parts of water. Subsequently, there were added 5.0 parts of 85% phosphoric acid and 4.1 parts of tellurium dioxide. The resultant mixture was evaporated to dryness over a water bath under agitation. The cake thus obtained was dried at 120°C, then pelleted and calcined at 500°C under air stream for 6 hours. The product thus obtained was used as the catalyst.

A mixed gas consisting of 5% of tert.-butyl alcohol, 12% of oxygen, 48% of nitrogen and 35% of steam (mol% all) was introduced as the raw material into a catalyst bed maintained at 380°C and allowed to react, with the contact time fixed at 3.6 seconds.

The reaction products were analyzed by gas chromatography and chemical analysis. The total of per-pass yield of methacrolein and methacrylic acid was found to be 74.0%.

EXAMPLE 2

In 600 parts of water, 38.5 parts of ammonium paratungstate was dissolved by boiling. To the resultant solution were added a solution having 35.3 parts of ammonium paramolybdate dissolved in 200 parts of water, a solution having 33.7 parts of iron nitrate and 8.3 parts of nickel nitrate dissolved in 200 parts of water and a solution having 4.14 parts of rubidium chloride dissolved in 50 parts of water. Then there was added 6.6 parts of 85% phosphoric acid. The resultant mixture was evaporated to dryness over a water bath under agitation. The cake was then calcined at 500°C under air stream for 6 hours. The calcined product was thoroughly mixed with 6.8 parts of tellurium dioxide added thereto and the mixture was pelleted and used as the catalyst. The reaction using this catalyst was carried out by repeating the procedure of Example 1, except that the temperature of the catalyst bed was kept at 375°C. Consequently the total of per-pass yield of methacrolein and methacrylic acid was 75.2%.

EXAMPLE 3

In 100 parts of water, 4.5 parts of ammonium paratungstate was dissolved. To the resultant solution were added a solution having 35.3 parts of ammonium paramolybdate dissolved in 200 parts of water, a solution having 4.8 parts of cobalt nitrate and 19.4 parts of nickel nitrate dissolved in 100 parts of water and a solution having 0.83 part of potassium nitrate and 0.05 part of rubidium chloride dissolved in 20 parts of water. Then, there were added a solution having 8.1 parts of bismuth nitrate dissolved in 60 parts of 10% nitric acid and 1.9 parts of 85% phosphoric acid. Subsequently 0.8 part of tellurium dioxide was added. Finally, 45 parts of 10% silica sol was added. The resultant mixture was evaporated to dryness over a water bath under agitation. The cake was dried at 120°C, pelleted and calcined at 500°C under air stream for six hours. The product thus obtained was used as the catalyst.

The reaction using this catalyst was carried out by repeating the procedure of Example 1, except that the temperature of the catalyst bed was fixed at 380°C. Consequently, the total of per-pass yield of methacrolein and methacrylic acid was 74.5%.

EXAMPLE 4

In 600 parts of water, 27.0 parts of ammonium paratungstate was dissolved. To the resultant solution were added a solution having 35.3 parts of ammonium paramolybdate dissolved in 200 parts of water and a solution having 13.5 parts of iron nitrate and 4.9 parts of nickel nitrate dissolved in 100 parts of water. Then, there were added a solution having 32.3 parts of bismuth nitrate dissolved in 150 parts of 10% nitric acid, a solution having 1.54 parts of potassium nitrate and 1.66 parts of cesium nitrate dissolved in 20 parts of water and 3.8 parts of 85% phosphoric acid. The resultant mixture was evaporated to dryness under agitation. The cake was then calcined at 500°C under air stream for six hours. The fired solid was thoroughly mixed with 5.6 parts of tellurium dioxide added thereto and the mixture was pelleted. The product thus obtained was used as the catalyst.

The reaction using this catalyst was carried out by repeating the procedure of Example 1, except that the temperature of the catalyst bed was fixed at 370°C. Consequently, the total of per-pass yield of methacrolein and methacrylic acid was 76.4%.

EXAMPLE 5

In 600 parts of water, 38.5 parts of ammonium paratungstate was dissolved by boiling. To the resultant solution were added a solution having 35.3 parts of ammonium paramolybdate dissolved in 200 parts of water, a solution having 2.7 parts of cobalt nitrate and 2.8 parts of nickel nitrate dissolved in 100 parts of water and a solution having 0.86 part of potassium nitrate dissolved in 20 parts of water. Then, there were added 5.0 parts of 85% phosphoric acid and 4.1 parts of tellurium dioxide. Finally a solution having 2.1 parts of stannous chloride dissolved in 20 parts of 10% nitric acid was added. The resultant mixture was evaporated to dryness over a water bath under agitation. The cake was dried at 120°C, thereafter pelleted and calcined at 500°C under air stream for six hours. The product thus obtained was used as the catalyst.

The reaction using this catalyst was carried out by repeating the procedure of Example 1, except that the temperature of the catalyst bed was fixed at 360°C. Consequently the total of per-pass yield of methacrolein and methacrylc acid was 76.0%.

EXAMPLE 6

In 600 parts of water, 38.5 parts of ammonium paratungstate was dissolved by boiling. To the resultant solution were added a solution having 35.3 parts of ammonium paramolybdate dissolved in 200 parts of water, a solution having 33.7 parts of iron nitrate and 8.3 parts of nickel nitrate dissolved in 200 parts of water and a solution having 0.07 part of potassium nitrate dissolved in 20 parts of water. Then, there was added 6.6 parts of 85% phosphoric acid. Finally a solution having 30.3 parts of stannous chloride dissolved in 300 parts of 10% nitric acid was added. The resultant mixture was evaporated to dryness over a water bath under agitation. The cake was calcined at 500°C under air stream for six hours. The calcined product was thoroughly mixed with 6.8 parts of tellurium dioxide added thereto, then pelleted and used as the catalyst. The reaction using this catalyst was carried out by repeating the procedure of Example 1, except that the temperature of the catalyst bed was fixed at 350°C. Consequently, the total of per-pass yield of mathacrolein and methacrylic acid was 78.3%.

EXAMPLE 7

In 100 parts of water, 4.5 parts of ammonium paratungstate was dissolved. To the resultant solution were added a solution having 35.3 parts of ammonium paramolybdate dissolved in 200 parts of water, a solution having 4.8 parts of cobalt nitrate and 19.4 parts of nickel nitrate dissolved in 100 parts of water and a solution having 1.26 parts of rubidium chloride dissolved in 20 parts of water. Then there were added a solution having 8.1 parts of bismuth nitrate dissolved in 60 parts of 10% nitric acid and 1.9 parts of 85% phosphoric acid. Further there were added 2.5 parts of stannic chloride and 0.8 part of tellurium dioxide. Finally 45 parts of 10% silica sol was added. The resultant mixture was evaporated to dryness. The cake was dried at 120°C, then pelleted and calcined at 500°C under air stream for six hours. The product thus obtained was used as the catalyst. The reaction using this catalyst was carried out by repeating the procedure of Example 1 except that the temperature of the catalyst bed was fixed at 365°C. Consequently the total of per-pass yield of methacrolein and methacrylic acid was 77.4%.

EXAMPLE 8

In 600 parts of water, 27.0 parts of ammonium paratungstate was dissolved. To the resultant solution were added a solution having 35.3 parts of ammonium paramolybdate dissolved in 200 parts of water, a solution having 13.5 parts of iron nitrate and 4.9 parts of nickel nitrate dissolved in 100 parts of water and a solution having 3.08 parts of potassium nitrate and 0.49 part of rubidium nitrate dissolved in 20 parts of water. Then there were added a solution having 32.3 parts of bismuth nitrate dissolved in 150 parts of 10% nitric acid and a solution having 1.9 parts of stannous chloride dissolved in 20 parts of 10% nitric acid. Finally, 3.8 parts of 85% phosphoric acid was added. The resultant mixture was evaporated to dryness. The cake was calcined at 500°C under air stream for six hours. The calcined product was thoroughly mixed with 5.6 parts of tellurium dioxide added thereto, then pelleted and used as the catalyst. The reaction using this catalyst was carried out by repeating the procedure of Example 1, except that the temperature of the catalyst bed was fixed at 365°C. Consequently, the total of per-pass yield of methacrolein and methacrylic acid was 78.8%.

EXAMPLE 9

In 50 parts of water, 2.25 parts of ammonium paratungstate was dissolved. To the resultant solution were added a solution having 35.3 parts of ammonium paramolybdate dissolved in 200 parts of water, a solution having 20.2 parts of iron nitrate and 43.7 parts of nickel nitrate dissolved in 500 parts of water and a solution having 0.21 parts of potassium nitrate and 0.66 part of cesium nitrate dissolved in 20 parts of water. Then there were added a solution having 16.2 parts of bismuth nitrate dissolved in 50 parts of 10% nitric acid and a solution having 3.8 parts of stannous chloride dissolved in 50 parts of 10% nitric acid. Finally, 1.9 parts of 85% phosphoric acid was added.

The resultant mixture was evaporated to dryness. The cake was calcined at 500°C under air stream for 6 hours. The calcined product was thoroughly mixed with 5.35 parts of tellurium dioxide added thereto, then pelleted and used as the catalyst. The reaction using this catalyst was carried out by repeating the procedure of Example 1, except that the temperature of the catalyst bed was fixed at 360°C. Consequently, the total of per-pass yield of methacrolein and methacrylic acid was 79.7%.

EXAMPLE 10

In 50 parts of water, 2.25 parts of ammonium paratungstate was dissolved. To the resultant solution was added a solution having 35.3 parts of ammonium paramolybdate dissolved in 200 parts of water. Then there were added 100 parts of silicon carbide and 4.9 parts of antimony oxide, a solution having 20.2 parts of ferric nitrate, 43.7 parts of nickel nitrate and 9.7 parts of cobalt nitrate dissolved in 500 parts of water, a solution having 0.257 part of potassium nitrate and 0.5 part of cesium nitrate dissolved in 10 parts of water, a solution having 16.2 parts of bismuth nitrate and 3.8 parts of stannous chloride dissolved in 50 parts of 10% nitric acid and a solution having 0.77 part of palladium nitrate dissolved in 20 parts of water in this order. Finally, 0.95 part of 85% phosphoric acid was added. Then the resultant mixture was evaporated to dryness. The cake was calcined at 500°C under air stream for five hours. The calcined product was thoroughly mixed with 5.35 parts of tellurium dioxide added thereto, then pelleted and used as the catalyst.

The reaction using this catalyst was carried out by repeating the procedure of Example 1, except that the temperature of the catalyst bed was fixed at 340°C. Consequently, the total of per-pass yield of methacrolein and methacrylic acid was 85.7%.

EXAMPLE 11

A catalyst was prepared by repeating the procedure of Example 10, except for omission of the addition of palladium nitrate and cobalt nitrate. The reaction using this catalyst was carried out by repeating the procedure of Example 1, except that the temperature of the catalyst bed was fixed at 370°C. Consequently, the total of per-pass yield of methacrolein and methacrylic acid was 84.2%.

EXAMPLE 12

In 600 parts of water, 27.0 parts of ammonium paratungstate was dissolved. To the resultant solution was added 4.9 parts of antimony oxide. Then there were further added a solution having 35.3 parts of ammonium paramolybdate dissolved in 200 parts of water and a solution having 13.5 parts of ferric nitrate and 4.9 parts of nickel nitrate dissolved in 100 parts of water. Thereafter, there were added a solution having 32.3 parts of bismuth nitrate dissolved in 150 parts of 10% nitric acid, a solution having 1.24 parts of potassium nitrate dissolved in 20 parts of water, a solution having 1.92 parts of palladium nitrate dissolved in 50 parts of water and 3.8 parts of 85% phosphoric acid in this order. The resultant mixture was evaporated to dryness. The cake was then calcined at 500°C under air stream for five hours.

The calcined product was thoroughly mixed with 5.6 parts of tellurium dioxide added thereto and thereafter the mixture was pelleted. This was used as the catalyst. The results are shown in the table attached at the end of this specification.

EXAMPLE 13

A catalyst was prepared by repeating the procedure of Example 12, except for omission of the addition of palladium nitrate.

EXAMPLE 14

In 100 parts of water, 4.5 parts of ammonium paratungstate was dissolved. To the resultant solution were added 100 parts of silicon carbide, 4.9 parts of antimony oxide and 0.88 part of germanium dioxide. There was further added a solution having 35.3 parts of ammonium paramolybdate dissolved in 200 parts of water. A solution having 4.8 parts of cobalt nitrate and 19.4 parts of nickel nitrate dissolved in 100 parts of water and a solution having 0.6 part of rubidium chloride and 1.0 part of cesium nitrate dissolved in 20 parts of water were added. Subsequently, there were added a solution having 8.1 parts of bismuth nitrate dissolved in 60 parts of 10% nitric acid and 1.0 part of 85% phosphoric acid. Finally, 25 parts of stannic oxide and 0.8 part of tellurium dioxide were added. The resultant mixture was evaporated to dryness. The cake was dried at 130°C for 16 hours, then pelleted, and calcined at 500°C under air stream for 5 hours. The product thus obtained was used as the catalyst.

EXAMPLE 15

A catalyst was prepared by repeating the procedure of Example 14, except for omission of the addition of germanium dioxide.

EXAMPLE 16

In 600 parts of water, 38.5 parts of ammonium paratungstate was dissolved by boiling. To the resultant solution were added 7.3 parts of antimony oxide and 50 parts of silicon carbide powder. Then there were further added a solution having 35.3 parts of ammonium paramolybdate dissolved in 200 parts of water, a solution having 33.7 parts of ferric nitrate and 8.3 parts of nickel nitrate dissolved in 200 parts of water, a solution having 4.2 parts of uranyl nitrate dissolved in 20 parts of water, a solution having 0.26 part of potassium nitrate, 0.30 part of rubidium nitrate and 0.50 part of cesium nitrate dissolved in 10 parts of water and 6.6 parts of 85% phosphoric acid in this order. Finally, a solution having 7.5 parts of stannous chloride dissolved in 100 parts of water was added. The resultant mixture was evaporated to dryness. The cake was calcined at 500°C under air stream for five hours. The calcined product was thoroughly mixed with 6.8 parts of tellurium dioxide added thereto. The resultant mixture was pelleted and used as the catalyst.

EXAMPLE 17

A catalyst was prepared by repeating the procedure of Example 16, except for omission of the addition of uranyl nitrate.

EXAMPLE 18

In 600 parts of water, 38.5 parts of ammonium paratungstate was dissolved by boiling. To the resultant solution were added 100 parts of silicon carbide, 0.69 part of antimony oxide, 0.38 part of titanium dioxide and 0.25 part of germanium dioxide. Then, there were further added a solution having 5 parts of ammonium paramolybdate dissolved in 200 parts of water, a solution having 2.7 parts of cobalt nitrate and 2.8 parts of nickel nitrate dissolved in 100 parts of water and a solution having 0.23 part of cesium nitrate dissolved in 10 parts of water. Subsequently, 5.0 parts of 85% phosphoric acid was added. Finally, a solution having 1.58 parts of stannous chloride dissolved in 50 parts of water was added. The resultant mixture was evaporated to dryness. The cake was then calcined at 500°C under air stream for 5 hours. The calcined product was thoroughly mixed with 4.1 parts of tellurium dioxide added thereto, then pelleted and used as the catalyst.

EXAMPLE 19

A catalyst was prepared by repeating the procedure of Example 18, except for omission of the addition of titanium dioxide and germanium dioxide.

The reaction was performed with each of the catalysts of Example 12 through 19 by repeatng the procedure of Example 1, except for the temperature of catalyst bed.

Table

| Example No. | Catalyst | Reaction temperature (°C) | Total of perpass yield of methacrolein and methacrylic acid (%) |
|---|---|---|---|
| 12 | P.Mo.W.Te.Sb.Ni.Fe.K.Bi.Pd | 330 | 84.1 |
| 13 | P Mo W Te Sb Ni Fe K Bi | 350 | 76.0 |
| 14 | P Mo W Te Sb Sn Ni Rb Cs Bi Co Ge | 345 | 83.9 |
| 15 | P Mo W Te Sb Sn Ni Rb Cs Bi Co | 370 | 82.5 |
| 16 | P Mo W Te Sb Sn Ni Fe K Rb Cs U | 340 | 84.3 |
| 17 | P Mo W Te Sb Sn Ni Fe K Rb Cs | 360 | 83.0 |
| 18 | P Mo W Te Sb Sn Ni Cs Co Ti Ge | 325 | 83.8 |
| 19 | P Mo W Te Sb Sn Ni Cs Co | 350 | 80.6 |

What is claimed is:

1. A method for the production of methacrolein and methacrylic acid, which comprises: contacting a mixed gas containing tertbutyl alcohol and oxygen with a calcined catalyst consisting essentially of the following composition in the vapor phase at a temperature in the range from 200° to 500°C:

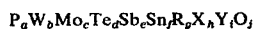

$$P_aW_bMo_cTe_dSb_eSn_fR_gX_hY_iO_j$$

wherein, R represents one of the combinations (a) Ni and Co, (b) Ni and Fe, (c) Ni, Co and Bi and (d) Ni, Fe and Bi; X represents K, Rb and/or Cs; Y represents Pd, U, Ge and/or Ti; $a,b,c,d,e,f,g,h,i$ and $j$ represent the numbers of atoms of the respective elements; and if $b + c = 1$, then $a = 0-1$, $d = 0.001 - 1$, $e = 0.01 - 0.8$, $f = 0-1$, $g = 0.08 - 2$, $h = 0.0005 - 0.5$, $i = 0-2$, and $j$ is a value automatically determined by the valencies of the metallic oxides present therein, the ratio of $b$ to $c$ is $0.01 - 100$ and the number of atoms of the two or three individual elements constituting R falls in the scope of $0.02 - 1$ when $b + c = 1$.

2. The method of claim 1, wherein the catalyst to be used has a composition such that $e = 0.01 - 0.8$ and $h = 0.0005 - 0.3$ where $b + c = 1$.

3. The method of claim 2, wherein the alkali metal represented by X is potassium and/or cesium.

4. The method of claim 1, wherein the catalyst to be used has a composition such that $e = 0.01 - 0.8$, $h = 0.0005 - 0.5$ and $f = 0.02 - 0.9$ where $b + c = 1$.

5. The method of claim 1, wherein the catalyst to be used has a composition such that $e = 0.01 - 0.8$, $h = 0.0005 - 0.5$ and $i = 0.01 - 1.6$ where $b + c = 1$.

6. The method of claim 1, wherein the catalyst to be used has a composition such that $e = 0.01 - 0.8$, $h = 0.0005 - 0.5$, $f = 0.02 - 0.9$ and $i = 0.01 - 1.6$ where $b + c = 1$.

* * * * *